(12) United States Patent
Lanz et al.

(10) Patent No.: US 9,408,682 B2
(45) Date of Patent: Aug. 9, 2016

(54) ANIMAL IMAGING HOLDING DEVICE AND METHOD

(75) Inventors: Titus Lanz, Rimpar (DE); Michael Sauer, Rimpar (DE)

(73) Assignee: RAPID BIOMEDICAL GMBH, Rimpar (DE)

( * ) Notice: Subject to any disclaimer, the term of this patent is extended or adjusted under 35 U.S.C. 154(b) by 1482 days.

(21) Appl. No.: 12/430,487

(22) Filed: Apr. 27, 2009

(65) Prior Publication Data

US 2010/0269260 A1 Oct. 28, 2010

(51) Int. Cl.
*A61D 3/00* (2006.01)
*A61B 5/055* (2006.01)
*A61B 6/03* (2006.01)

(52) U.S. Cl.
CPC ............... *A61D 3/00* (2013.01); *A61B 5/0555* (2013.01); *A61B 6/03* (2013.01); *A61B 2503/40* (2013.01)

(58) Field of Classification Search
CPC ...................................................... A61D 3/00
USPC ......... 119/420, 751, 752, 753, 755, 757, 174, 119/417, 418; 5/284, 421, 422, 423, 601; 219/217
See application file for complete search history.

(56) References Cited

U.S. PATENT DOCUMENTS

| | | |
|---|---|---|
| 4,721,060 A | 1/1988 | Cannon et al. |
| 4,860,741 A | 8/1989 | Bernstein et al. |
| 5,099,792 A | 3/1992 | Cannon et al. |
| 5,297,502 A | 3/1994 | Jaeger |
| 5,896,829 A | 4/1999 | Rothenberg et al. |
| 6,006,524 A * | 12/1999 | Park ................................. 62/3.7 |
| 6,651,587 B1 | 11/2003 | DeFord et al. |
| 6,776,158 B1 | 8/2004 | Anderson et al. |
| 6,904,912 B2 | 6/2005 | Roy et al. |
| 7,377,276 B2 | 5/2008 | Roy et al. |
| 2004/0187216 A1* | 9/2004 | Lin ..................................... 5/706 |
| 2004/0216737 A1 | 11/2004 | Anderson et al. |
| 2007/0169717 A1 | 7/2007 | Conger et al. |
| 2007/0175404 A1 | 8/2007 | Conger et al. |
| 2007/0244422 A1 | 10/2007 | Chiodo |
| 2008/0047554 A1 | 2/2008 | Roy et al. |
| 2008/0168951 A1 | 7/2008 | Starr et al. |
| 2009/0084378 A1* | 4/2009 | Ichikawa ................. 128/203.12 |
| 2010/0198047 A1* | 8/2010 | Zagorchev et al. ........... 600/411 |

FOREIGN PATENT DOCUMENTS

WO 2007135248 A1 11/2007

OTHER PUBLICATIONS

English-language translation of WO 2007135248 A1.*

* cited by examiner

*Primary Examiner* — Lisa Tsang
(74) *Attorney, Agent, or Firm* — Pearne & Gordon LLP (57) ABSTRACT

A device and a method for imaging an animal including an animal holding device for keeping the animal immobile and at a desired temperature during the scanning operation for imaging the animal in real-time in a non-destructive manner.

38 Claims, 8 Drawing Sheets

Figure 6

ANIMAL IMAGING HOLDING DEVICE AND METHOD

BACKGROUND OF THE INVENTION

This application relates generally to an animal holding device for holding an animal during an imaging operation.

More specifically, this application relates to an apparatus and method of heating an animal holding device for keeping the animal immobile at a desired temperature during a scanning operation for imaging the animal in real-time in a non-destructive manner.

Rodents and other laboratory animals are often used for testing purposes. Such testing may involve the need to scan the animal using a scanning device, such as an SPECT, PET, CT, CAT, X-Ray, NMR/MR, or other imaging device, to provide real time and/or photographic images of the animal, which may be done in a non-destructive manner. It may be desirable to anesthetize such animals in order to completely immobilize the animal during the scanning process. Anesthetized animals, and in particular rodents, often cannot hold their body temperature at desired temperatures during such procedures, potentially leading to stress on the animal.

Thus, desirable is a system and method of maintaining the body temperature of immobilized animals in a consistent state while the animal is being anesthetized and/or while the animal is being scanned, or otherwise utilized by the testing process.

Also desirable is a device for supporting the anesthetizing and scanning process that is compatible with those functions and the devices supporting such functions.

Furthermore, in particular for NMR applications, heating systems that are fully compatible with the imaging technology to avoid interference in the scanning process are needed. Classical methods such as water pipes or electrical heating blankets either are NMR visible, or interact with the RF field of the NMR system.

SUMMARY OF THE INVENTION

Provided are a plurality of embodiments the invention, including, but not limited to, an animal holding device for holding an animal in a condition for imaging the animal, with the animal holding device comprising: a housing; an animal bed adapted to fit in a first portion of the housing; a holding unit for holding the animal in a relatively fixed position, the holding unit being adapted to fit into a second portion of the housing; and a heater adapted to fit into a third portion of the housing. The heater is adapted to heat unheated air, received from an air pump provided external to the housing, via an air conduit, and the animal bed is formed with one or more internal channels adapted for circulating heated air received from the heater through the channels for heating the bed. The animal holding device is adapted to be placed into an imaging device for imaging the animal.

Also provided is an animal holding device for holding an animal in a condition for imaging the animal, with the animal holding device comprising: an elongated housing having a width and a length that is much more than the width; an animal bed adapted to fit in a first portion of the housing, the animal bed comprising a first channel and a second channel; a holding unit for holding the animal in a relatively fixed position, the holding unit being adapted to fit into a second portion of the housing and being adapted for providing anesthesia to the animal prior to and/or during the imaging; and a heater adapted to fit into a third portion of the housing and also adapted for heating fluid received from a fluid pump. The animal bed is attached to the heater via a first conduit connected to the first channel for transmitting heated fluid to the animal bed from the heater, and the second channel is connected to a second conduit for removing the heated fluid from the animal bed. The animal holding device is adapted for being placed into an imaging machine for imaging the animal while the animal is anesthetized.

Still further provided is an animal holding device for holding a small rodent in a condition for imaging the rodent, with the animal holding device comprising: an elongated housing having a width and a length that is much more than the width, wherein the length is much larger than the length of the rodent; a removable and severable animal bed adapted to fit in a first portion of the housing, the animal bed comprising a first channel and a second channel embedded in the animal bed; a removable and severable holding unit for holding the head of the rodent in a relatively fixed position, the holding unit being adapted to fit into a second portion of the housing next to the first portion; a heater for providing heated air to the animal bed and adapted to fit into a third portion of the housing; and at least one sensor for obtaining temperature data about a temperature of the heated air. The temperature of the device is maintained by a controller utilizing the temperature data from the sensor for controlling the heater, such that the heater is adapted to heat unheated air received from an air pump via an air conduit, and the first channel of the animal bed is adapted for receiving heated air from the heater via a first conduit connected to the heater and the first channel, and the second channel is adapted to return at least a portion of the heated air to the heater via a second conduit for dissipation into an ambient surrounding of the animal holding device.

Further provided is an animal holding device for holding an animal in a condition for imaging the animal, the device comprising: a removable and severable animal bed comprising a first channel and a second channel embedded in the animal bed; a removable and severable holding unit for holding the head of the animal in a relatively fixed position, the holding unit being adapted to fit next to the animal bed; a heater for providing heating air to the animal bed; and at least one sensor for obtaining temperature data about a temperature of the heated air. The temperature is maintained by a controller utilizing the temperature data from the sensor for controlling the heater, and the heater is adapted to heat air received from an air pump via an air conduit. The first channel of the animal bed is adapted for receiving the heated air from the heater via a first conduit connected to the heater and the first channel, and the second channel is adapted to return at least a portion of the heated air to the heater via a second conduit for dissipation into an ambient surrounding of the animal holding device. Furthermore, the animal holding device has a width and a length that is much more than the width, wherein the length is substantially longer than the length of the animal.

Also provided is a method of imaging an animal, with the method comprising the steps of:
securing the animal to an animal bed installed in an animal holding device;
providing anesthesia to the animal during the securing;
providing air to a heater for heating the air to a controlled temperature;
providing the heated air at the controlled temperature to the animal bed;
circulating the heated air through the animal bed to keep a temperature of the animal in a desired range;
releasing the heated air to ambient after the circulating; and imaging the animal during the securing and the circulating by placing the animal holding device during the securing into an imaging device and performing the imaging.

Also provided are additional embodiments of the invention, some, but not all of which, are described hereinbelow in more detail.

BRIEF DESCRIPTION OF THE DRAWINGS

The features and advantages of the examples of the present invention described herein will become apparent to those skilled in the art to which the present invention relates upon reading the following description, with reference to the accompanying drawings, in which:

FIG. 3AA shows a partially internal view of the heater of FIG. 3A;

FIG. 3B' shows a schematic view of the bottom of the animal bed of FIG. 3B;

FIG. 3BB shows a perspective view of the top of the animal bed of FIG. 3B;

DETAILED DESCRIPTION OF THE EXAMPLE EMBODIMENTS

Examples of a system and method of heating and holding animals in an immobile or partially immobile state, in particular animals such as rodents, for medical and experimental scanning purposes, such as NMR scanning, for example, is disclosed.

Figure 1:
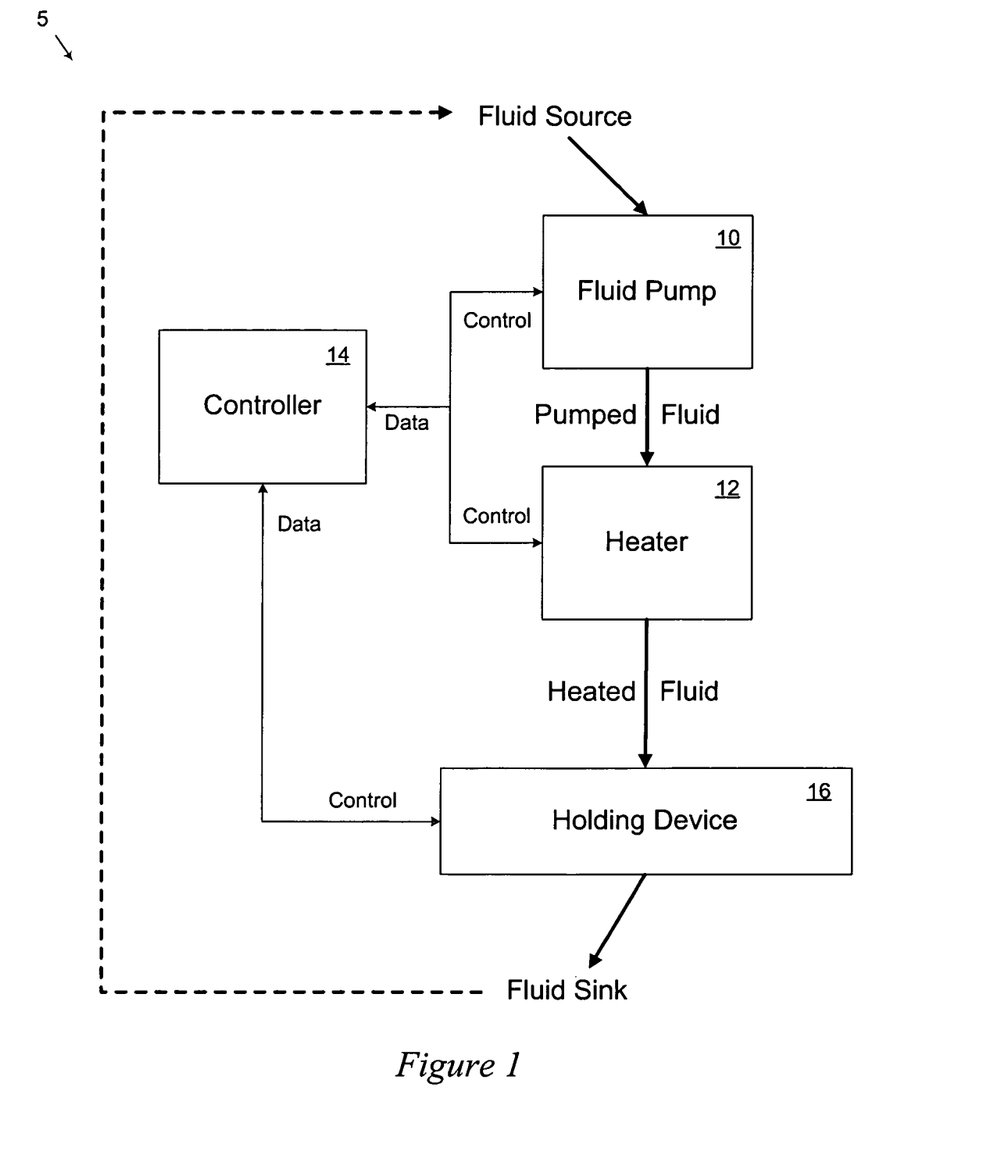
FIG. 1 is a block diagram showing an example generic setup for an animal holding device having a heating function.

Generally, the system includes a scanning apparatus and a animal holding system 5 including a fluid pump 10, a heater 12, a controller 14, and an animal holding device 16 for holding the animal, as shown by the block diagram of FIG. 1. The controller 14 is utilized to control the operation of the fluid pump 10 and the heater 12, and potentially the other components of the control unit, via control lines. The fluid pump 10 obtains the heating fluid from a source, pumps the heating fluid to the heater 12, and then the heated fluid is further pumped to the animal holding device 16, where it is utilized for heating the interior of the chamber that holds the animal. The fluid is then exhausted from the animal holding device, and in some embodiments it may be re-circulated to the source for reuse, resulting in a closed, or partially closed, system. Various ones of these components might be left out for some embodiments, or substitutions provided therefore, and thus this generalized example is merely illustrative of one possible such system.

In a first example embodiment specifically designed for use with small rodents as test animals, described in more detail below, air is used as the heating fluid, with the source of the air being the ambient atmosphere, which also becomes the ultimate sink for the exhausted heated air. However, alternative embodiments could use other working fluids, such as water, nitrogen, a refrigerant, steam, or any other useful fluid (gas or liquid, or some combination of the two, including two-phase systems) that can be circulated through the device. Although alternative embodiments are not shown or described in the same level of detail as the first example embodiment, the principles utilized for the first example embodiment can be utilized for other embodiments as well by adapting the various components to the particular application. Some of these potential modifications are discussed below.

Because the chosen working fluid for the first example embodiment is air, it is possible that this fluid (air) could be blown directly over the animal to keep the animal warm. However, in order to avoid dehydration of the animal, the heated air, which tends to be dry, is preferably not directly blown over the animal. Instead, the heated fluid can be circulated through an animal bed that is provided for the animal to be laid upon, heating the animal bed, and thus indirectly heating the animal and avoiding dehydration of the animal. If air were chosen to be blown over the animal, it might be preferable to add moisture to the heated air to avoid or minimize dehydration, but this would add additional equipment and cost to the device, and thus for many or most situations would not be preferable.

A useful option would be to include embodiments that are not bound to a dedicated animal heating chamber. In NMR imaging, the sample is typically excited with a homogeneous magnetic RF field and detected using a sensitive receive RF coil. The transmit coil, in some applications, may be relatively large. With no loss of available space, the transmit resonator can be heated (such as by utilizing mostly cylindrical housings, therefore covering the whole area around the animal and thereby heating the whole environment). Therefore, precious space in the heating chamber is not wasted on an extra heating chamber which could make the setup more expensive. The larger the magnet bore has to be, the more expensive is the magnet (the main cost factor for NMR systems). Although this may save only an inch or two, such space savings can be precious to the researcher.

Figure 2:
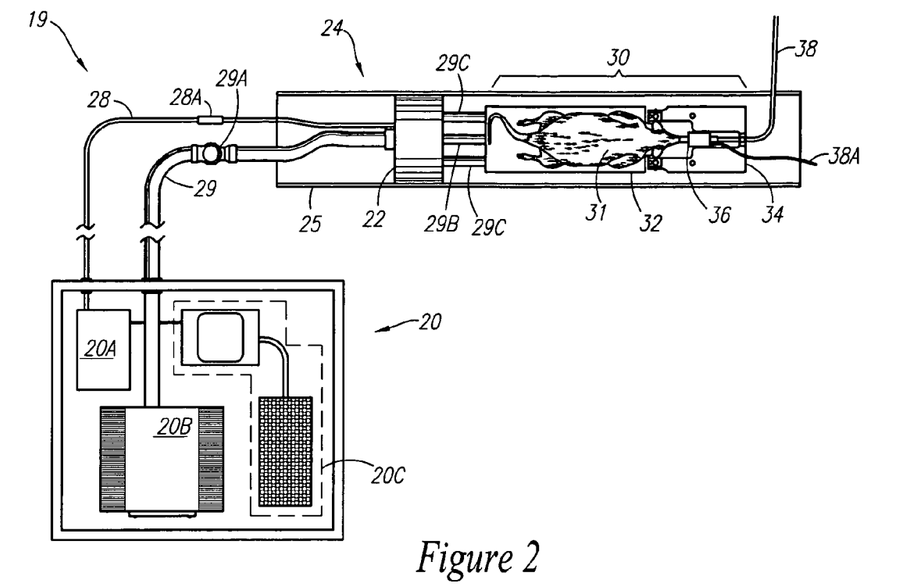
FIG. 2 is a schematic diagram showing a first example embodiment of the animal holding device with a control unit.

The animal holding system 19 shown schematically in FIG. 2 is a first example embodiment of the generic system for use with small rodents. A controller 20A and a fluid pump 20B are provided in a control unit 20 separate from the system 19. The control unit 20 also has a power supply 20C for generating a current for the heater and for the internal components of the control unit 20.

An elongated animal holding device 24 (shown in more detail in FIG. 3) has an elongated housing 25, and is connected to the control unit 20 via electrical (e.g., wires) and fluid (e.g., hollow conduits/tubes) connections 28, 29 respectively. The animal holding device 24 includes a preferably removable heater 22 embedded in the housing 25, although non-removable heaters could also be utilized where beneficial. Making the heater removable could provide economic benefits by allowing fewer heaters to be used for more devices, putting them in place only when needed. It also allows different types of heaters to be substituted for each other, if desired. Furthermore, embodiments without the housing 25 could be prepared by merely connecting the various internal components together (i.e., the heater 22, animal bed 32, and/or the holding unit 34), potentially further reducing the costs. These connections could be provided by using tongue and groove or tab/slot connections between the components, for example.

An electrical cable 28 with disconnectable coupler 28A provides power and control leads to the heater 22 from the power supply 20C embedded in the control unit 20, and an air tube/conduit 29 with disconnectable coupler 29A provides air as the heating fluid to the heater 22 from the fluid pump embedded in the control unit 20.

The animal holding device 24 also includes a holding chamber 30 provided within the housing 25 for holding an animal 31, with the holding chamber being comprised of a removable animal bed 32 for the animal 31 to be laid upon, and a removable holding unit 34 for helping to hold the animal in place and having a snout chamber 36 adapted for receiving the snout of the animal.

Heated air is provided from the removable heater 22 into the animal bed 32 via feed tube/conduit 29B. The heated air is circulated through the animal bed 32 and returned to the heater 22 by return tube(s)/conduit(s) 29C, where the returned air is dissipated into the ambient environment, and at the same time can be utilized for cooling the surface of the heater housing, which may reach temperatures of about 60° C. The animal bed 32 is heated by the heated air that is circulated within, and which thereby heats the animal chamber 30 and/or the animal itself (such as by the processes of convection and/or radiation, for example). The various tube/conduits discussed in the disclosure could be constructed from any of a number of components, such as PVC tubing, rubber hoses, or other appropriate mediums.

The fluid pump 20B could be implemented with a magnetic air pump, which can be provided in the control unit 20. Typically, magnetic pumps are avoided for NMR applications due to potential magnetic interference or damage to the NMR device, but by placing the pump at some distance from the animal holding device, and thus some distance from the NMR imaging device, with the heater provided near or in the animal holding device, such interference can be minimized or eliminated.

The heater 22 might be located at a distance of about 20 cm to the animal region of interest (ROI), for example, thus keeping temperature losses at a minimum, thereby avoiding the use of isolation tubes, which would typically be too massive for routine use on small animal handling systems such as the one in the first example embodiment. Providing the heater at about such a distance from the ROI also helps to cut down on potential electrical interference during the scanning process. In contrast, the fluid pump 20B (and thus the control unit 20 as well when the pump is integrated therein) may be placed several meters from the ROI to avoid any magnetic interference with the scanner, for example. If the heater is to be placed with the pump, in further contrast, the conduit transmitting the heated fluid (e.g., air) would likely need to be insulated to avoid excessive heat losses.

Figure 4:
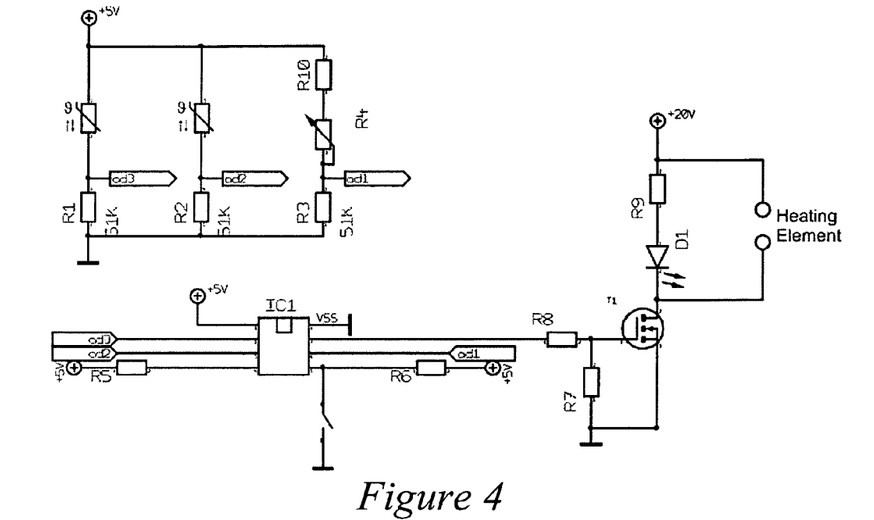
FIG. 4 shows an example control circuit for controlling the heater of FIG. 3A.

The controller 20A could be comprised of a microcontroller acting as proportional plus integral controller, such as one utilizing the circuit of FIG. 4, for example. Temperature measurements can be provided by sensors provided at some point in the heater, or after the heater, such as in the holding device itself or in the conduits or at their junctions. For the first example embodiment, two NTC Sensors are utilized in the heater 22. One sensor can be utilized for measuring the actual temperature of the backflow (returned heated air provided by return tube(s)/conduit(s) 29C), while another sensor can be used as an overheating watchdog (e.g., limit 60° C.) by measuring the heated air (provided to the feed tube/conduit 29B). The temperature of the heater can be adjusted via pulse-width modulation of the power supplied to the heater, for example. The set-point of the back flow temperature (which should almost equal the heated chamber temperature) can be, for example, set in a range between 32° C. and 40° C. For an example application, in combination with a heated chamber volume of 100 cm3 (e.g., for a rat bed), the 37° C. rise time is about 4 minutes (for 39° C., about 5 min). Total temperature oscillation stability can be reached after about 10 minutes, or even faster.

Figure 3:
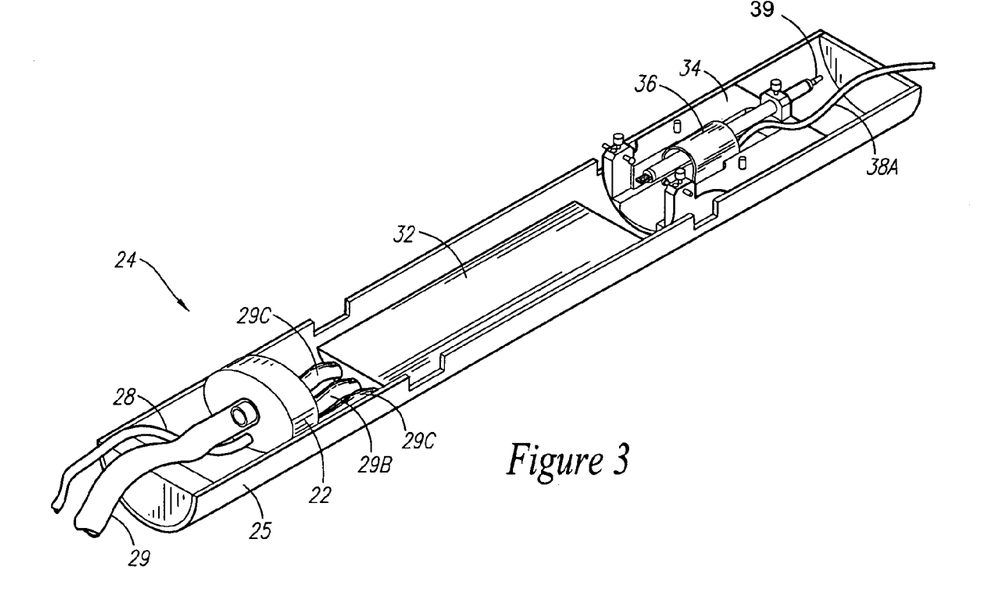
FIG. 3 is a perspective view of the animal holding device of the first example embodiment.
Figures 3, 3A:
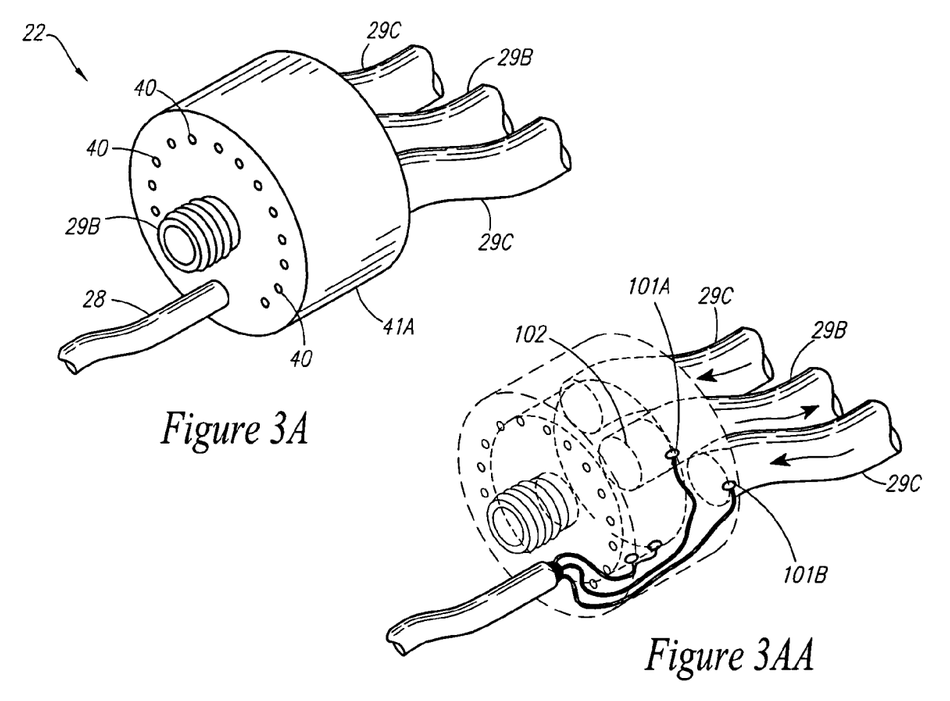
FIG. 3A shows a perspective view of a heater for use with the first example embodiment of the animal holding device.
Figures 3, 3B:
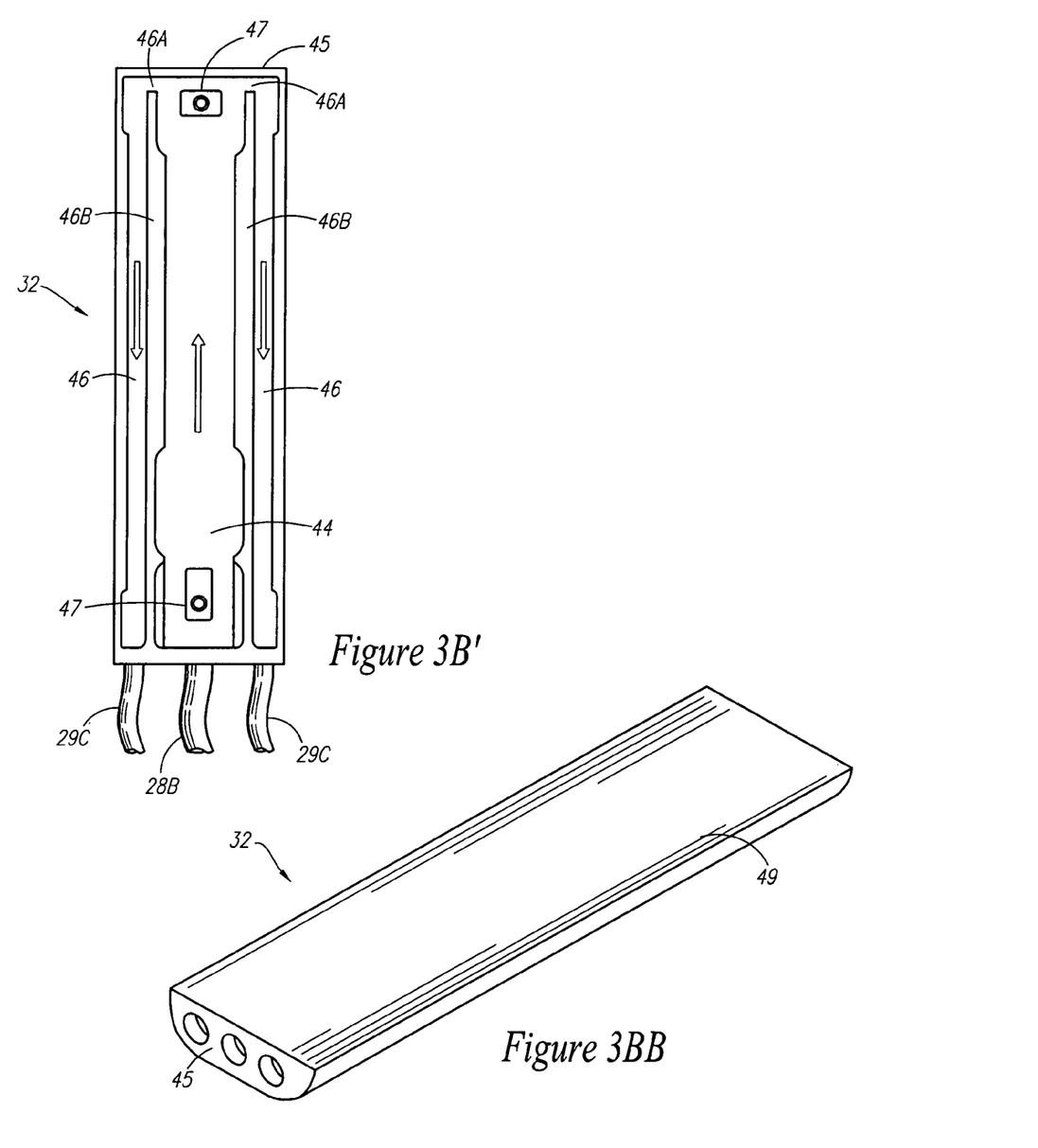
FIG. 3B shows a perspective view of the bottom of an animal bed for use with the first example embodiment of the animal holding device.
Figure 3B:
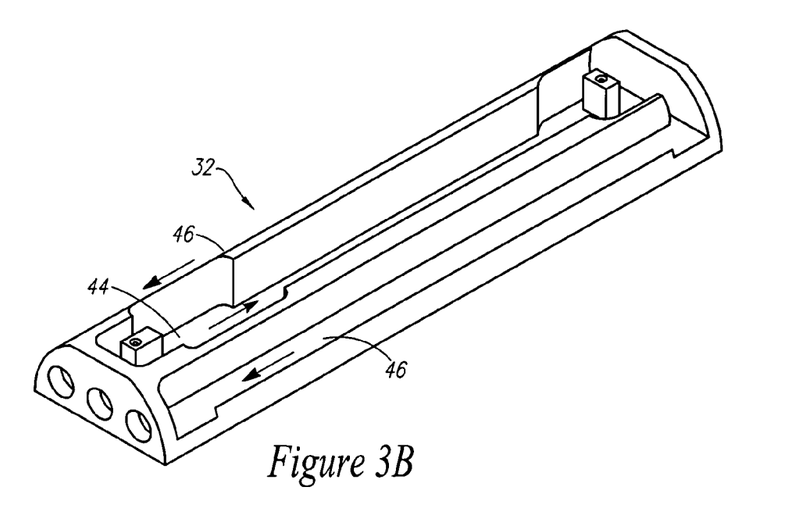
Figure 3C:
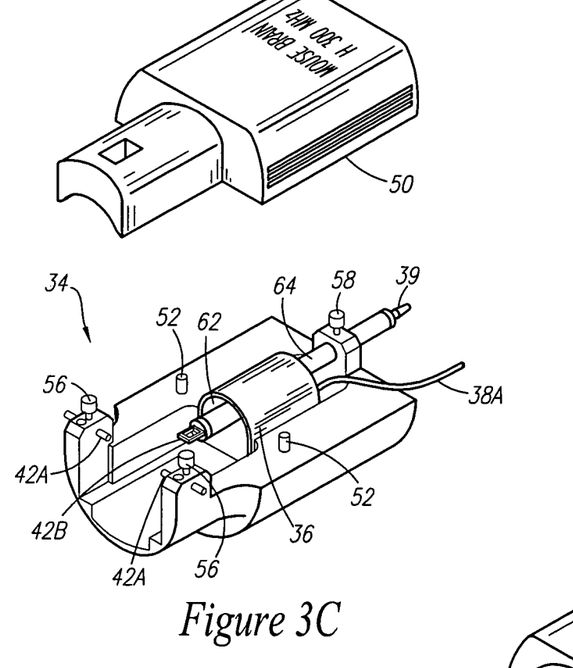
FIG. 3C shows a first animal holding unit adapted for holding a mouse and for use with the first example embodiment of the animal holding device.

As shown in more detail in FIG. 3, the animal holding device 24 of the first example embodiment is comprised of a housing 25, a heater 22 shown in more detail in FIG. 3A, an animal bed 32 shown inverted and in more detail in FIG. 3B, and a holding unit 34 shown in more detail in FIG. 3C.

The heater 22, shown in more detail in the example heater 41A of FIG. 3A, can be made from perforated BaTiO3 ceramics, for example. The heater 22 can be passed by the backflowing air via return tube(s)/conduits(s) 29C to prevent an overheating of the components of the device (and keep the surface of the heater 22 cooler than it otherwise would be without the backflow, for example, to protect users of the device and/or the animal). The returned air can then be dissipated into ambient through holes 40 provided in the heater 22 as shown in FIG. 3A. Alternatively, the returned air might be re-circulated through the air pump, if desired, perhaps for energy savings or for applications using a different working fluid.

FIG. 3AA shows an internal view of the heater 22 of the first example embodiment, with heating element 102 for heating the air, sensor 101A for sensing the temperature of the source heated air being provided to the animal bed 32 via feed tube/conduit 29B, and/or a sensor 101B for sensing the temperature of the returning air returned by one of the return tube(s)/conduit(s) 29C. Additional sensors could be utilized, such as by providing a sensor for both return tubes/conduits, for example, or a single sensor might be utilized at any of these locations. Furthermore, one or more sensors might be added to monitor the body temperature of the animal, or its respiration, or other animal bodily functions as well.

The housing 25, the animal bed 32, and the holding unit 34 are preferably made of an electromagnetic transparent medium, preferably a plastic such as PVC or polycarbonate (PC). Referring to FIG. 3B and FIG. 3B', the animal bed 32 is provided with one or more channels 44, 46 through which the heated fluid (in this example, "air") can flow in the direction of the arrows, with a single feed channel 44 and two return channels 46 shown being utilized for the first example embodiment, although a single pair of channels might be utilized for the circulation. The channels can be formed by using a hollow frame 45 with walls 46B provided as shown. The channels are connected in a manner such that the heated fluid (air) will flow back and forth through the animal bed, such as by forming gaps 46A in the walls 46B, for example. For another example, the channels might be formed into an "oval" or pair of "ovals" pattern by connecting them with a curved section(s), or it may utilize more angular connections as shown in the example embodiments of FIGS. 3B, 3B'. In this manner, the heated air circulates through the animal bed 32 to keep the bed, and thus the animal, at a desired temperature to avoid stressing the animal. The animal is placed on the flat portion 49, as shown in FIG. 3BB. The bed channels 44, 46 can be closed, or kept open as shown in the examples, but being effectively closed when the animal bed 22 is installed in the housing 25, which can be by securing the posts 47 to the housing 25, for example.

The channels 44, 46 of the animal bed 32 should be designed to facilitate the transfer of heat from the heated air to the bed to improve the heat transfer efficiency. This can be accomplished by using a large surface area of the heating chamber internal to the bed, using a plurality of channels as snake-like paths for the air flow, for example, or by making the walls of the bed relatively thin to allow better heat transfer. Utilizing materials having a good heat transfer characteristic might also be utilized.

FIG. 3C shows the holding unit 34 in more detail, including a body, animal ear holding hardware 42A and teeth holding hardware 42B for holding the animals' head immobile, and including a snout cover 48 provided in the snout chamber for placing in communication with the animal's nose (e.g., snout) via the hollow opening 62 for connecting to a gas tube/conduit that is connected to connector 39 for providing a gas or gasses to the animal through the tube 64, such as anesthesia and/or oxygen or other gas or gasses for affecting or defining the state and/or maintaining the health of the animal. These gasses can then be returned (e.g., "sucked out") by return tube/conduit 38A. These structures are particularly useful for animals who are rodents (such as rats and mice, for example), but they could be adapted to be utilized for other animals as well utilizing different holding structures, such as those that might squeeze the animal's skull in a vice-like grip, for example. In addition, the body of the animal may also be held in place by various structures, such as straps or grips for holding the legs or body of the animal, for example. Alternatively, the gasses could be provided through the tube of the teeth holding hardware, and provided directly to the mouth or nose of the animal, or a hood of some sort could be used to cover the snout of the animal to encase the gas or gasses around the snout.

Figure 3D:
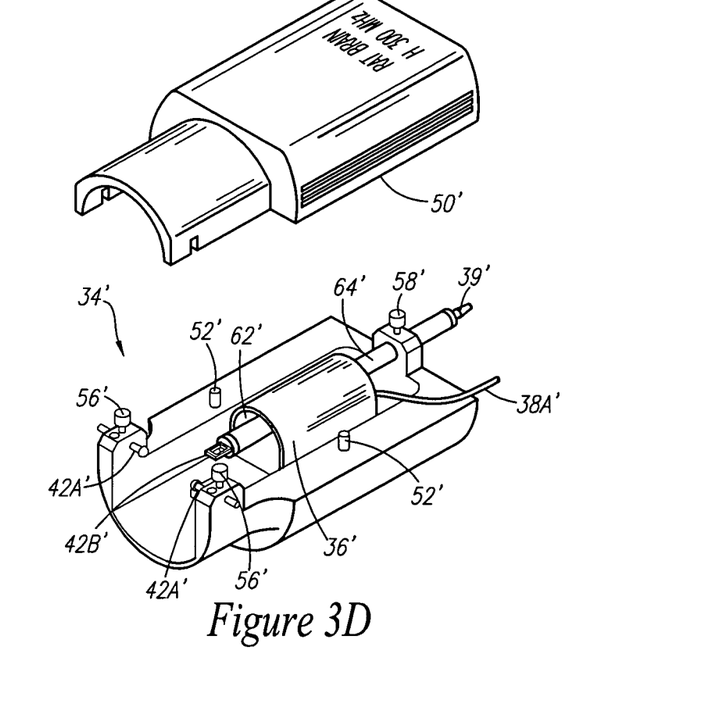
FIG. 3D shows a second animal holding unit adapted for holding a rat and for use with the first example embodiment of the animal holding device.
Figure 6:
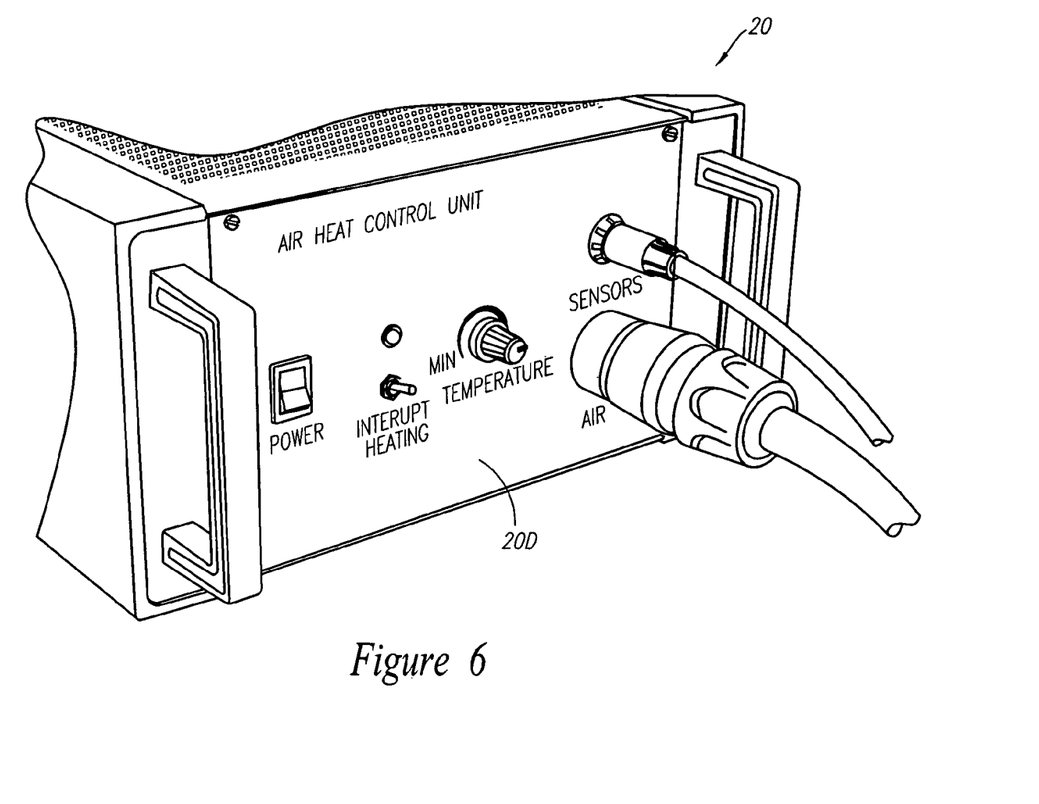
FIG. 6 shows a control interface of the control unit for controlling the first example embodiment of the animal holding device.

The holding unit 34 shown in FIG. 3C is designed for holding a mouse, whereas an alternative holding unit 34' is shown in FIG. 3D is designed for holding a rat, which is a larger rodent. Covers 50 and 50' can be provided including head coils in support of NMR scanning operations, and can be held in place utilizing tabs 52, 52' with corresponding recesses in the covers (not shown). The covers would be placed over the heads of the animals prior to the scanning operation. FIG. 6 shows an example embodiment of a control faceplate of the control unit 20 that can be utilized for entering the various settings of the system via the controls on the control panel 20D.

The holding unit 34 of the example can be adjusted to the particular animal by using adjusting fixtures 56, 56' to adjust the length of the ear holders 42A and 42A', respectively, to fit the particular animal. Similarly, tubes 64, 64' can be moved axially by adjusting fixtures 58, 58' and pulling the tubes 64, 64' in order to pull the snout of the rodent into the snout cover 36, 36' to properly administer the desired gasses through the tubes 64, 64'. The snout cover 36, 36' can also be slid along the holding unit to further adjust the device to the particular animal, as well.

The animal holding device of the first example embodiment is optimized for rat brain and mouse brain imaging (thus the head coils 50, 50'). For that purpose, the scan times are several minutes, while the image resolution is typically far below 1 mm. This typically requires that a substantial effort be spent on immobilizing the head of the animal. This is done in the first example embodiment by holding the head at three points on the bone: the teeth and the two ears (such as via the ear canals), which typically does not harm the animal. Rat heart imaging, in contrast, typically only requires holding the teeth of the animal (a bite bar) for keeping the position of the animal constant in a longitudinal direction, and thus holding the ears in place (using the ear sticks) is not necessary for such an application. Other applications might utilize similar, or different, holding mechanisms.

The holding unit, the animal bed, and the heater are preferably provided as separate and severable components as shown in the first example embodiment (described above) so that they can be separately provided and exchanged for each other, if desired, in order to increase adaptability of the device, such that different holding unit designs could be matched with various different animal beds and/or heaters in various combinations in order to increase the utility of the device for different types and/or sizes of animals, for example. Nevertheless, it would be possible to integrate any two of these units, or all three of these units, if such flexibility is not desirable or integration is otherwise preferable for a particular implementation.

A cover for the animal holding device could be provided to cover the entire animal, or even the entire animal holding device or portion thereof, prior to, during, and/or after imaging, if desired, but such a cover might not be necessary for all applications, and none is shown for the first example embodiment of the device. Instead, only head covers having RF coils are shown for utilizing the animal holding device for brain imaging.

The device can be utilized by placing the animal, which preferably was anesthetized in advance, within the animal chamber of the device with the animal body resting on the animal bed and securing the animal's head with the holding unit. In the case of a rodent, the head can be held in place by placing the teeth of the animal in a hole in the teeth holding hardware, and placing tabs of the ear holding hardware inserted into the animal's ear. These devices are then adjusted to immobilize the head of the animal. The snout cover can be placed over the snout of the animal to feed one or more gasses to the respiratory system of the animal to anesthetize the animal and/or keep it oxygenated or otherwise in a desired state. Gasses for other purposes can also be provided.

Figure 5:
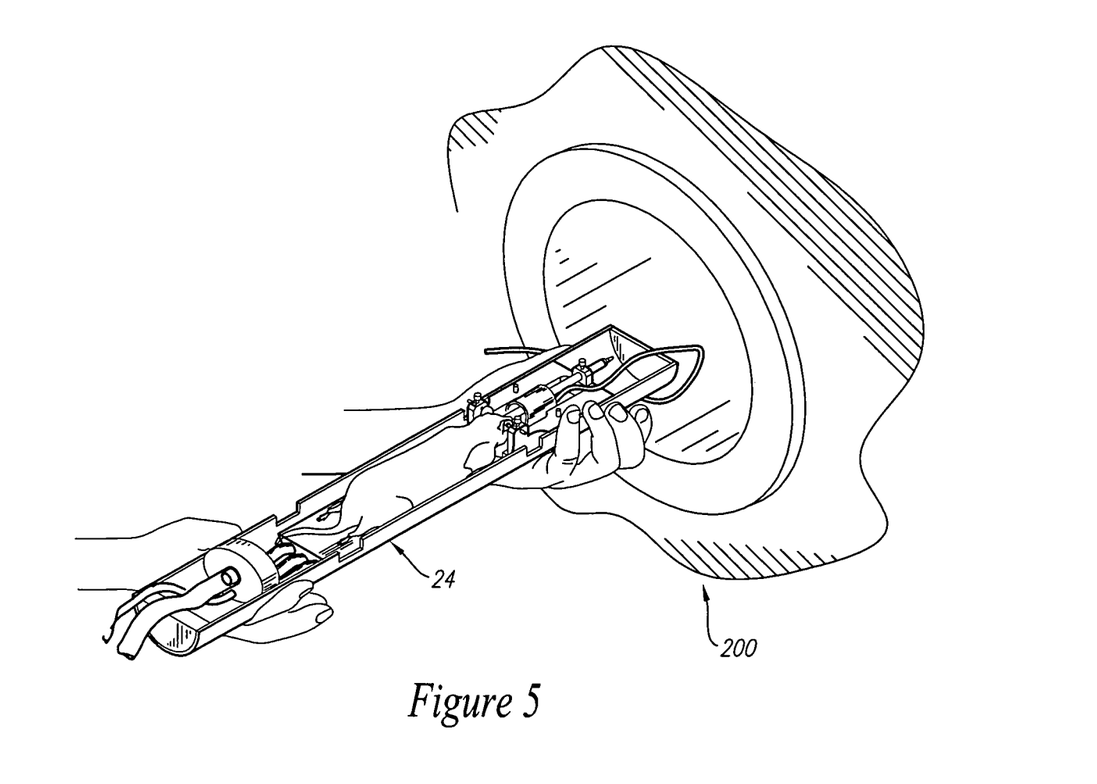
FIG. 5 shows the process of inserting the animal holding device, holding an animal, into a scanning machine for imaging the animal.

The anesthetized and immobilized animal can then be scanned by inserting at least a portion of the animal holding device 24 holding the animal into an imaging machine 200, such as, for example, an NMR imaging machine, as shown in example of FIG. 5 for the first example embodiment of the device, and then activating the imaging process with the animal immobilized and stable. Note that head coils are not shown installed in this figure, but could be utilized where desired (such as for brain scanning operations) by covering the heads of the rodents prior to scanning. The holding device can then be removed when the imaging is complete, and the animal can be revived, removed, and/or replaced, if desired. Alternatively, the holding device might be placed on a surface and an imaging scanner passed over the holding device. Other alternative methods of scanning can also be utilized, as desired, because the animal holding device is adaptable for a variety of applications and uses.

NMR imaging utilizing the animal holding device 24 of the first example embodiment shows no interaction of the heating system with imaging (gradient eddy currents, vibrations, B1-distortions etc).

Figure 7:
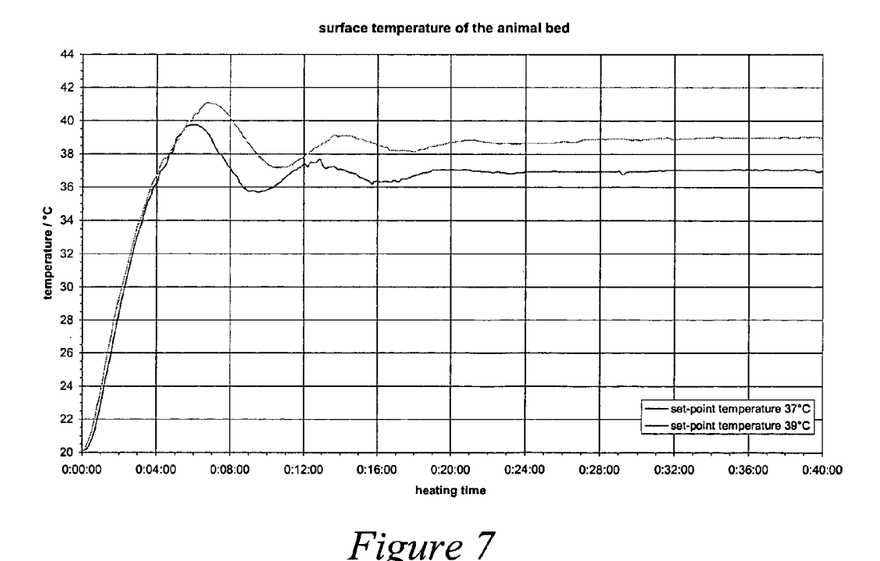
FIG. 7 is a plot of temperature settling times for the first example embodiment using a particular control scheme.

The animal heating system of the first example embodiment for NMR scanning is based on the use of warm air flow. Testing shows that the method comes along without or with few imaging artifacts. Due to heating the animal chamber, the animal does not dehydrate and remains in low stress. The settling time can be reduced by directly controlling the temperature of the animal bed. Future development will be using different heated chambers for different applications. For example, controlling the temperature of the transmit volume resonator will spare extra heated chambers and save precious space. FIG. 7 shows a plot of surface temperatures of the animal bed for the first example embodiment at a setpoint of 37° C. and another plot at a setpoint of 39° C.

Alternative embodiments could be provided for larger animals, such as for rabbits, dogs, cats, or other animals, by scaling some of the features and adapting others of the features, as required. For example, a much larger device could be utilized for rabbits or cats, for example, by increasing the size of the animal bed, and utilizing a different holding device adapted for the specific animal, such as a vice for immobilizing the skull of the animal, and/or straps for holding the body and legs in place, for example.

The invention has been described hereinabove using specific examples and embodiments; however, it will be understood by those skilled in the art that various alternatives may be used and equivalents may be substituted for elements and/or steps described herein, without deviating from the scope of the invention. Modifications may be necessary to adapt the invention to a particular situation or to particular needs without departing from the scope of the invention. It is intended that the invention not be limited to the particular implementations and embodiments described herein, but that the claims be given their broadest interpretation to cover all embodiments, literal or equivalent, disclosed or not, covered thereby.

What is claimed is:

1. An animal holding device for holding an animal in a condition for imaging the animal, said device comprising:
    a housing;
    an animal bed;
    a holding unit for holding the animal in a relatively fixed position, said holding unit being placed in front of said animal bed; and
    a heater placed behind said animal bed, wherein
    said heater is adapted to heat unheated air, received from an air pump provided external to said housing, via an air conduit, and further wherein
    said animal bed is formed with one or more internal channels adapted for circulating heated air received from said heater through said channels for heating said bed, wherein
    said animal holding device is adapted to be placed into an imaging device for imaging the animal.

2. The animal holding device of claim 1, wherein said holding unit is further adapted for providing anesthesia to the animal prior to and/or during said imaging.

3. The animal holding device of claim 2, wherein said holding unit is further adapted to hold the animal by including a means of securing one or both of the animal's front teeth, or the animal's ears or ear canals.

4. The animal holding device of claim 1, wherein said animal bed, said holding unit, and said heater are separable from each other.

5. The animal holding device of claim 1, wherein said animal bed and said holding unit are integrated together.

6. The animal holding device of claim 1, wherein said holding unit is further adapted to hold the animal by including a means of securing the animal's front teeth or a means of securing the animal's ears or ear canals or both.

7. The animal holding device of claim 1, further comprising an elongated housing in which said animal bed, said holding unit, and said heater are placed, such that a length of said elongated housing is much more than a width of said housing.

8. The animal holding device of claim 7, wherein any cross section of said housing across said width forms a curved portion and a straight portion, and wherein said straight portion is open to an ambient surrounding for accepting said animal bed, said holding unit, and said heater.

9. The animal holding device of claim 8, wherein said cross section of said housing is substantially semi-circular such that said housing resembles half an elongated hollow cylinder cut along its axis.

10. The animal holding device of claim 9, wherein said animal holding device resembles said half of the elongated cylinder with said animal bed and said holding device installed.

11. The animal holding device of claim 8, wherein said animal bed, said holding unit, and said heater are each separately removable from said housing.

12. The animal holding device of claim 1, wherein said one or more internal channels are adapted to return said heated air to said heater for dissipation into an ambient surrounding of said animal holding device while also cooling an outer surface of said heater.

13. The animal holding device of claim 12, wherein said animal bed is connected to said heater via at least one conduit for receiving said heated air from said heater, and wherein said animal bed is also connected to said heater via at least one additional conduit for returning said heating air to said heater, wherein said at least one or more channels includes at least one channel connected to said conduit for said receiving said heated air, wherein said at least one channel is connected to at least one other channel connected to said additional conduit for returning at least a portion of said heated air.

14. The animal holding device of claim 13, wherein an additional channel is provided in said animal bed, with the channel being connected to said at least one channel for returning another portion of said heated air to said heater via an additional conduit.

15. The animal holding device of claim 1, further comprising a sensor for obtaining temperature data about a temperature of said heated air, wherein said temperature is maintained by a controller utilizing said temperature data from said sensor for controlling said heater.

16. The animal holding device of claim 15, wherein said sensor is provided to measure a temperature of said heated air that is being returned to said heater from said bed, said device further providing an additional sensor to detect a temperature of said heated air prior to said heated air being provided to said animal bed, said additional sensor being provided to said animal bed for providing additional temperature data to said controller.

17. The animal holding device of claim 1, wherein said device is adapted for holding a small rodent.

18. An imaging system comprising the animal holding device of claim 1 and also comprising said air pump, wherein said air pump is a magnetic air pump that is located a sufficient distance from said animal imaging device during said imaging to avoid substantially interfering with said imaging.

19. An animal holding device for holding an animal in a condition for imaging the animal, said device comprising:
    an elongated housing having a width and a length that is much more than said width;
    an animal bed adapted to fit in a first portion of said housing, said animal bed comprising a first channel and a second channel;

a holding unit for holding the animal in a relatively fixed position, said holding unit being adapted to fit into a second portion of said housing and being adapted for providing anesthesia to the animal prior to said imaging, during said imaging, or both; and a heater adapted to fit into a third portion of said housing and also adapted for heating fluid received from a fluid pump; wherein the entirety of said animal bed is provided between said heater and said holding unit, and is attached to said heater via a first conduit connected to said first channel for transmitting heated fluid to said animal bed from said heater, and still further wherein said second channel is connected to a second conduit for removing at least a portion of the heated fluid from said animal bed, and wherein said animal holding device is adapted for being placed into an imaging machine for imaging the animal while the animal is anesthetized.

20. The animal holding device of claim 19, wherein said fluid is air.

21. The animal holding device of claim 20, wherein said second conduit is connected to said heater for returning said heated air to said heater from said animal bed for dissipation into an ambient surrounding while also cooling the outer surface of said heater.

22. A system comprising said animal holding device of claim 19 further including at least one sensor for obtaining temperature data about a temperature of said heated air, and also comprising a control unit including:
   said fluid pump,
   a controller utilizing said temperature data from said sensor for controlling said heater, and
   a control interface for allowing a user to control said heating.

23. The system of claim 22, wherein said second conduit is connected to said heater for returning heated air to said heater from said animal bed for dissipation into an ambient surrounding.

24. The system of claim 22, wherein said fluid pump is a magnetic fluid pump that is located some distance from said animal imaging device during said imaging.

25. The animal holding device of claim 19, wherein said animal bed further comprises a third channel for removing another portion of the heated fluid from said animal bed.

26. An animal holding device for holding a small rodent in a condition for imaging the rodent, said device comprising:
   an elongated housing having a width and a length that is much more than said width, wherein said length is much larger than the length of said rodent;
   a removable and severable animal bed adapted to fit in a first portion of said housing, said animal bed comprising a first channel and a second channel embedded in said animal bed;
   a removable and severable holding unit for holding the head of the rodent in a relatively fixed position, said holding unit being adapted to fit into a second portion of said housing next to said first portion;
   a heater for providing heated air to said animal bed and adapted to fit into a third portion of said housing; and
   at least one sensor for obtaining temperature data about a temperature of said heated air, wherein said temperature is maintained by a controller utilizing said temperature data from said sensor for controlling said heater, wherein
   said heater is adapted to heat unheated air received from an air pump via an air conduit, and further wherein
   said first channel of said animal bed is adapted for receiving said heated air from said heater via a first conduit connected to said heater and said first channel, and still further wherein
   said second channel is adapted to return at least a portion of said heated air to said heater via a second conduit for dissipation into an ambient surrounding of said animal holding device.

27. The animal holding device of claim 26, wherein a third channel is provided in said animal bed connected to said first channel for returning another portion of said heated air to said heater via a third conduit.

28. The animal holding device of claim 26, wherein said at least one sensor is placed to detect a temperature of said heated air prior to said heated air being provided to said animal bed.

29. The animal holding device of claim 28, further providing another sensor to measure a temperature of said heated air being returned to said heater from said animal bed.

30. The animal holding device of claim 26, wherein said at least one sensor is for measuring a temperature of said heated air being returned to said heater from said animal bed.

31. A system comprising said animal holding device of claim 26 and further comprising a control unit including:
   said fluid pump,
   a controller utilizing said temperature data from said sensor for controlling said heater, and
   a control interface for allowing a user to control said heating.

32. The system of claim 31, wherein said fluid pump is a magnetic fluid pump that is located some distance from said animal imaging device during said imaging to avoid substantially interfering with said imaging.

33. An animal holding device for holding an animal in a condition for imaging the animal, said device comprising:
   a removable and severable animal bed comprising a first channel and a second channel embedded in said animal bed;
   a removable and severable holding unit for holding the head of the animal in a relatively fixed position, said holding unit being adapted to fit next to said animal bed;
   a heater for providing heating air to said animal bed; and
   at least one sensor for obtaining temperature data about a temperature of said heated air, wherein said temperature is maintained by a controller utilizing said temperature data from said sensor for controlling said heater, wherein
   said heater is adapted to heat air received from an air pump via an air conduit, and further wherein
   said first channel of said animal bed is adapted for receiving said heated air from said heater via a first conduit connected to said heater and said first channel, and still further wherein
   said second channel is adapted to return at least a portion of said heated air to said heater via a second conduit for dissipation into an ambient surrounding of said animal holding device.

34. An animal holding device for holding an animal in a condition for imaging the animal, said device comprising:
   a housing;
   an animal bed comprising a plurality of channels embedded in said animal bed, said housing being adapted to receive said animal bed in a removable manner;
   a holding unit for holding the head of the animal in a relatively fixed position, said holding unit being adapted to fit in front of said animal bed within said housing in a removable manner; and a heater for providing a heated fluid to said animal bed, said heater being adapted to fit behind said animal bed in said housing in a removable manner, such that said animal bed is provided between said holding unit and said heater, wherein said heater is adapted to heat said fluid received from a pump via a conduit, and further wherein said channels of said animal bed are adapted for receiving said heated fluid from said heater via a first conduit connected to said heater, and still further wherein said channels are adapted to return said fluid to said heater via a second conduit connected to said channels, and wherein said fluid is air taken from an ambient surrounding.

35. An animal holding device for holding a small rodent in a condition for imaging the rodent, said device comprising:

a housing;

a removable and severable animal bed adapted to fit in said housing;

a removable and severable holding unit separate from said animal bed for holding the head of the rodent in a relatively fixed position, said holding unit being adapted to fit into said housing;

a heater for providing heated air to said animal bed, said heater also adapted to fit into said housing; and at least one sensor provided near said heater in said housing, said sensor for obtaining temperature data about a temperature of said heated air, wherein said heater is adapted to heat said bed using air in an open loop manner.

36. An animal holding device for holding an animal in a condition for imaging the animal, said device comprising:

a removable animal bed comprising at least one channel embedded in said animal bed;

a removable holding unit for holding the head of the animal in a relatively fixed position, said holding unit being adapted to fit next to said animal bed;

a removable heater for providing heated air to said at least one channel of said animal bed, wherein said heater is adapted to heat unheated air received from an air pump via an air conduit connected to an ambient surrounding of said air pump, and further wherein at least one of said at least one channel of said animal bed is adapted for receiving said heated air from said heater for heating said bed, and still further wherein said heated air is transported from at least one of said at least one channel for dissipation into an ambient surrounding of said animal holding device.

37. The animal holding device of claim 36, wherein said heated air returned from said animal bed back to said heater is used for cooling said heater.

38. An animal holding device for holding an animal in a condition for imaging the animal, said device comprising:

a removable animal bed comprising at least one channel embedded in said animal bed;

a removable holding unit for holding the head of the animal in a relatively fixed position, said holding unit being adapted to fit next to said animal bed;

a removable heater for providing heated air to said at least one channel of said animal bed, wherein said heater is adapted to heat unheated air received from an ambient surrounding, and further wherein at least one of said at least one channel is adapted for receiving said heated air from said heater for heating said bed, and still further wherein at least one of said at least one channel is adapted to return said heated air from said animal bed back to said heater for cooling said heater where said heater is adapted for dissipating the returned heated air into an ambient surrounding of said animal holding device at said heater.

* * * * *